United States Patent [19]
Koike et al.

[11] Patent Number: 5,766,911
[45] Date of Patent: Jun. 16, 1998

[54] MUTATED FARNESYLDIPHOSHATE SYNTHASE CAPABLE OF SYNTHESIZING GERANYLGERANYLDIPHOSPHATE AND GENE CODING THEREFOR

[75] Inventors: Ayumi Koike, Toyota, Japan; Shusei Obata, New York, N.Y.; Tokuzo Nishino, Sendai, Japan; Shinichi Ohnuma, Sendai, Japan; Takeshi Nakazawa, Sendai, Japan; Kyozo Ogura, Sendai, Japan; Tanetoshi Koyama, Sendai, Japan

[73] Assignee: Toyota Jidosha Kabushiki Kaisha, Toyota, Japan

[21] Appl. No.: 534,910

[22] Filed: Sep. 28, 1995

[30] Foreign Application Priority Data

Feb. 14, 1995 [JP] Japan .................... 7-025253

[51] Int. Cl.$^6$ .................... C12N 9/10; C12N 15/54; C12N 15/70; C12P 19/44
[52] U.S. Cl. .................... 435/193; 435/75; 435/69.1; 435/172.3; 435/252.3; 435/252.33; 435/320.1; 536/23.2
[58] Field of Search .................... 435/69.1, 172.3, 435/193, 252.3, 252.33, 320.1, 75; 536/23.2

[56] References Cited

FOREIGN PATENT DOCUMENTS

| | | |
|---|---|---|
| 0537553 | 4/1993 | European Pat. Off. |
| 0 674 000 A2 | 9/1995 | European Pat. Off. |
| 0699761 | 3/1996 | European Pat. Off. |
| 5-219961 | 8/1993 | Japan . |
| 91/13078 | 9/1991 | WIPO . |
| 96/21736 | 7/1996 | WIPO . |

OTHER PUBLICATIONS

Math, et al., *Proc. Natl. Acad. Sci. USA*, vol. 89, Aug. 1992, pp. 6761–6764.

Hoshino, et al., *Appl. & Envir. Mic.*, 59:9 Sep. 1993, pp. 3150–3153.

Journal Of Bacteriology, vol. 154, No. 2, pp. 580–590, May 1983, Dean P. Taylor et al.:*Alignment of Genetic and Restriction Maps of the Photosynthesis Region of theRhodopseudomonas capsulataChromosome by a Conjugation–Mediated Maker Rescue Technique.*

Science, vol. 229, (1985), pp. 242–247, Richard M. Myers et al.: *A General Method for Saturation Mutagenesis of Cloned DNA Fragments.*

J. Biochem., vol. 113, (1993), pp. 355–363, T. Koyama et al.: *Thermostable Farnesyl Diphospahate Synthase ofBacillus stearothermophilus: Molecular Cloning, Sequence Determination, Overproduction, and Purification.*

Molecular and Cellular Biology, vol. 7, No. 9, (1987), pp. 3138–3146, Catherine F. Clarke et al.: *Molecular Cloning and Sequence of a Cholesterol–Repressible Enzyme Related to Prenyltransferase in the Isoprene Biosynthetic Pathway.*

J. Biochem., vol. 108, (1990), pp. 995–1000, Shingo Fujisaki et al.: *Cloning and Nucleotide Sequence of the ispA Gene Responsible for Farnesyl Diphosphate Synthase Activity inEscherichia coli.*

J. Biological Chemistry, vol. 264, (1989), pp. 19176–19184, Matt S. Anderson et al.: *Farnesyl Diphosphate Synthetase— Molecular Cloning, Sequence, and Expression of an Essential Gene FromSaccharomyces Cerevisiae.*

J. Biological Chemistry, vol. 265, No. 8, (1990), pp. 4607–4614, Douglas J. Wilkin et al.: *Isolation and Sequence, of the Human Farnesyl Pyrophosphate Synthetase cDNA.*

(List continued on next page.)

*Primary Examiner*—Robert A. Wax
*Assistant Examiner*—William W. Moore
*Attorney, Agent, or Firm*—Kenyon & Kenyon

[57] ABSTRACT

A mutated farnesyldiphosphate synthase capable of synthesizing geranylgeranyldiphosphate and gene coding for said mutated enzyme, wherein the mutated enzyme is modified from a native farnesyldiphosphate synthase by mutation of a gene coding for a native farnesyldiphosphate synthase.

29 Claims, 9 Drawing Sheets

OTHER PUBLICATIONS

J. Bacteriology, vol. 172, No. 12, (1990), pp. 6704–6712, Norihiko Misawa et al.: *Elucidation of theErwinia uredovoraCarotenoid Biosynthetic Pathway by Functional Analysis of Gene Products LExpressed inEscherichia coli*.

J. Biological Chemistry, vol. 269, No. 20, (1994), pp. 14792–14797, Shin–ichi Ohnuma et al.: *Archaebacterial Ether–linked Lipid Biosynthetic Gene*.

Tohoku Regional Meeting Of Allied Association Of Academic Associations in Chemical Field, 30 Sep. 1995, Shinichi Ohnuma et al.: *Modification of Catalitic Function of Farnesyldi–phosphate Synthase by Random Mutagenesis*.

Fig. 2

A (1) MAQLSVEQFLNEQKQAVETALSRYIERLEGPAKLKKAM　　　　　　　　　　A YSLEAGGKRIRPL LLLST
(2) MDFPQQLEACVKQANQALSRFIAPLPFQNTPVVETM　　　　　　　　　　　Q YGALLGGKRLRPF LVYAT
(3) MASEKEIRRERFLNVFPKLVEELNASLLAYGMPKEACDWYAHS　　　　　　　LNY NTPGGKLNRGL SVVDT
(4) MNGDQNSDVYAQEKQDFVQHFSQIVRVLTEDEMGHPEIGDAIARLKEV　　　LEY NAIGGKYNRGL TVVVA
(5) MNGDQKLDVHNQEKQNFIQHFSQIVKVLTEDELGHPEKGDAITRIKEV　　　LEY NTVGGKYNRGL TVVQT

B (1) VRALGKDPAVGLPVA　　　　　　　　　　　　　　　CAI EMIHT YSLIHDDLPSMONDDLRRGKPTN HKVFGEAMAIL
(2) GHMFGVSTNTLDAPAAAVE　　　　　　　　　　　　 C I H AYSLIHDDLPAMDDDLRRGLPTC HVKFGEANAIL
(3) YAILSNKTVEQLGQEEYEKVAILGW　　　　　　　　　C I ELLQ AYFLVDD MMDKSITRRGQP C WYKVPEVGEI
(4) FRELVEPRKQDADSLQRAWTVGW　　　　　　　　　　C VELLQ AFFLVADD IMDSSLTRRGQ TC WYQKPGVGLD
(5) FQELVEPRKQDAESLQRALTVGW　　　　　　　　　　C VELLQ AFFLVLDD IMDSSHTRRGQI C WYQKPGIGLD

C                                                                                  D (1)　A GDG    LLTYA    FQLITEIDDERIPPSVRLRLIERLAKAAGPEGMVA    GQAADM  EGEGKTLTLSE
(2)　A GDALQTL     A    FSILSDADMPEVSDRDRISMISELASASGIAGMCG    GQALDL  DAEGKHVPLDA
(3)　AINDAF   ML  EA   AIYKLLKSHFRNEKYYIDITELFHEVTFQTEL       GQLMDL  ITAPEDKVDLS
(4)　AINDAN   LL  EA   CIYRLLKLYCREQPYYLNLIELFLQSSYQTEI       GQTLDL  LTAPQGNVDLV
(5)　AINDAL   LL  EA   AIYRLLKFYCREQPYYLNLIELFLQSSYQTEI       GQTLDL  ITAPQGGVDLG

|     |                |                                      |                   |
|-----|----------------|--------------------------------------|-------------------|
| (1) | LEYIHRH        | KTGKMLQYSVHAG ALIG G ADAR QTRELDEFAAHL |                   |
| (2) | LERIHRH        | KTGA LIRAAVRLGALS AG DKG RRALPVLDKYAESI |                  |
| (3) | KFSLKKHSFIVTF  | KTAYYSFYLPVAL AMYVAGITDEK DLKQARDVLIPL |                  |
| (4) | RFTEKRYKSIVKY  | KTAFYSFYLPIAA AMYMAGI D G EKEHANAKKILLEM |                |
| (5) | RYTEKRYKSIVKY  | KTAFYSFYLPIAA AMYMAGI D G EKEHANALKILLEM |                |

F

|     |                                                                                                |
|-----|------------------------------------------------------------------------------------------------|
| (1) | GLAFQIRDDILDIEGAEEKI GKPVGSD QSNNKAT YPAALLSLAGAKEKLAFHIEAAQRHLRNADVDGAA                        |
| (2) | GLAFQVQDDILDVVGDTA TLGKRQGAD QQLGK S TYPALLGLEQARKKARDLIDDARQSLKQLAEQSLDTS                      |
| (3) | GEYFQIQDDYLDCFGTPEQI GKI GTDIQDN KCS WVINKALELASAEQRKTLDENYGKKDSVAEAKCKKIF                      |
| (4) | GEFFQIQDDYLDLFGDPSVT GKI GTDIQDN KCS WLVVQCLQRATPEQYQILKENYGQKAEKVARVKALYE                      |
| (5) | GEFFQIQDDYLDLFGDPSVT GKV GTDIQDN KCS WLVVQCLLRATPQQRQILEENYGQKDPEKVARVKALY                      |

G

|     |   |                              |
|-----|---|------------------------------|
| (1) | L | AYICELVAARDH                 |
| (2) |   | LEA LADYIIQRNK               |
| (3) |   | LTAFLN KVYKRSK               |
| (4) |   | LG LARKIYKRRK                |
| (5) |   | LE LANKIYKRRK                |

|     |                                      |
|-----|--------------------------------------|
| (1) | A                                    |
| (2) | NDLKIEQLYHEYEESIAKDLKAKISQVDESRGFKADV |
| (3) | ELDLPAVFLQYEEDSYSHIMALIEQYAAPLPPAVF   |
| (4) | EELDLRSVFFKYEEDSYNRLKSLIEQCSAPLPPSIF  |
| (5) | EELDLRSVFFKYEEDSYNRLKSLIEQCSAPLPPSIF  |

(1) B. STEAROTHERMOPHILAS
(2) E. COLI
(3) YEAST
(4) HUMAN
(5) RAT

Fig. 4

```
                  2                            34
W.T    1 : MAQLSVEQFLNEQKQAVETALSRYIERLEGPAKLKKAMAYSLEAGGKRIR
No.1   1 :
No.2   1 :                    V
No.3   1 :
No.4   1 :

59                    81
W.T   51 : PLLLLSTVRALGKDPAVGLPVACAIEMIHTYSLIHDDLPSMDNDDLRRGK
No.1  51 :                             H
No.2  51 :         Q
No.3  51 :
No.4  51 :                             H

141
W.T  101 : PTNHKVFGEAMAILAGDGLLTYAFQLITEIDDERIPPSVRLRLIERLAKA
No.1 101 :
No.2 101 :
No.3 101 :
No.4 101 :

157               182
W.T  151 : AGPEGMVAGQAADMEGEGKTLTLSELEYIHRIIKTGKMLQYSVHAGALIGG
No.1 151 :
No.2 151 :
No.3 151 :    A                     Y
No.4 151 :

239
W.T  201 : ADARQTRELDEFAAHLGLAFQIRDDILDIEGAEEKIGKPVGSDQSNNKAT
No.1 201 :
No.2 201 :
No.3 201 :
No.4 201 :                            R 265       275
W.T  251 : YPALLSLAGAKEKLAFHIEAAQRHILRNADVDGAALAYICELVAARDHX
No.1 251 :                S
No.2 251 :
No.3 251 :
No.4 251 :                   T
```

5,766,911

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 894 base pairs
        ( B ) TYPE: nucleic acid
        ( C ) STRANDEDNESS: double
        ( D ) TOPOLOGY: linear ( i i ) MOLECULE TYPE: DNA ( v i ) ORIGINAL SOURCE:
        ( A ) ORGANISM: Bacillus stearothermophilus ( x i ) SEQUENCE DESCRIPTION: SEQ ID NO:1:

```
ATGGCGCAGC TTTCAGTTGA ACAGTTTCTC AACGAGCAAA AACAGGCGGT GGAAACAGCG    60
CTCTCCCGTT ATATAGAGCG CTTAGAAGGG CCGGCGAAGC TGAAAAAGGC GATGGCGTAC   120
TCATTGGAGG CCGGCGGCAA ACGAATCCGT CCGTTGCTGC TTCTGTCCAC CGTTCGGGCG   180
CTCGGAAAAG ACCCGGCGGT CGGATTGCCC GTCGCCTGCG CGATTGAAAT GATCCATACG   240
CACTCTTTGA TCCATGATGA TTTGCCGAGC ATGGACAACG ATGATTTGCG GCGCGGCAAG   300
CCGACGAACC ATAAAGTGTT CGGCGAGGCG ATGGCCATCT TGGCGGGGGA CGGGTTGTTG   360
ACGTACGCGT TTCAATTGAT CACCGAAATC GACGATGAGC GCATCCCTCC TTCCGTCCGG   420
CTTCGGCTCA TCGAACGGCT GGCGAAAGCG GCCGGTCCGG AAGGGATGGT CGCCGGTCAG   480
GCAGCCGATA TGGAAGGAGA GGGGAAAACG CTGACGCTTT CGGAGCTCGA ATACATTCAT   540
CGGCATAAAA CCGGGAAAAT GCTGCAATAC AGCGTGCACG CCGGCGCCTT GATCGGCGGC   600
GCTGATGCCC GGCAAACGCG GGAGCTTGAC GAATTCGCCG CCCATCTAGG CCTTGCCTTT   660
CAAATTCGCG ATGATATTCT CGATATTGAA GGGGCAGAAG AAAAAATCGG CAAGCCGGTC   720
GGCAGCGACC AAAGCAACAA CAAAGCGACG TATCCAGCGT TGCTGTCGCT TGCCGGCGCG   780
AAGGAAAAGT TGGCGTTCCA TATCGAGGCG GCGCAGCGCC ATTCACGGAA CGCCGACGTT   840
GACGGCGCCG CGCTCGCCTA TATTTGCGAA CTGGTCGCCG CCCGCGACCA TTAA          894
```

( 2 ) INFORMATION FOR SEQ ID NO:2:

( i ) SEQUENCE CHARACTERISTICS:
        ( A ) LENGTH: 894 base pairs
        ( B ) TYPE: nucleic acid
        ( C ) STRANDEDNESS: double
        ( D ) TOPOLOGY: linear ( i i ) MOLECULE TYPE: DNA (vi) ORIGINAL SOURCE:
 (A) ORGANISM: Bacillus stearothermophilus (xi) SEQUENCE DESCRIPTION: SEQ ID NO:2:

```
ATGGCGCAGC TTTCAGTTGA ACAGTTTCTC AACGAGCAAA AACAGGCGGT GGAAACAGCG    60
CTCTCCCGTT ATATAGAGCG CTTAGAAGGG CCGGCGAAGG TGAAAAAGGC GATGGCGTAC   120
TCATTGGAGG CCGGCGGCAA ACGAATCCGT CCGTTGCTGC TTCTGTCCAC CGTTCAGGCG   180
CTCGGCAAAG ACCCGGCGGT CGGATTGCCC GTCGCCTGCG CGATTGAAAT GATCCATACG   240
TACTCTTTGA TCCATGATGA TTTGCCGAGC ATGGACAACG ATGATTTGCG GCGCGGCAAG   300
CCGACGAACC ATAAAGTGTT CGGCGAGGCG ATGGCCATCT TGGCGGGGGA CGGGTTGTTG   360
ACGTACGCGT TTCAATTGAT CACCGAAATC GACGATGAGC GCATCCCTCC TTCCGTCCGG   420
CTTCGGCTCA TCGAACGGCT GGCGAAAGCG GCCGGTCCGG AAGGGATGGT CGCCGGTCAG   480
GCAGCCGATA TGGAAGGAGA GGGGAAAACG CTGACGCTTT CGGAGCTCGA ATACATTCAT   540
CGGCATAAAA CCGGGAAAAT GCTGCAATAC AGCGTGCACG CCGGCGCCTT GATCGGCGGC   600
GCTGATGCCC GGCAAACGCG GGAGCTTGAC GAATTCGCCG CCCATCTAGG CCTTGCCTTT   660
CAAATTCGCG ATGATATTCT CGATATTGAA GGGGCAGAAG AAAAAATCGG CAAGCCGGTC   720
GGCAGCGACC AAAGCAACAA CAAAGCGACG TATCCAGCGT TGCTGTCGCT TGCCGGCGCG   780
AAGGAAAAGT TGGCGTTCCA TATCGAGGCG GCGCAGCGCC ATTTACGGAA CGCCGACGTT   840
GACGGCGCCG CGCTCGCCTA TATTTGCGAA CTGGTCGCCG CCCGCGACCA TTAA         894
```

(2) INFORMATION FOR SEQ ID NO:3:

(i) SEQUENCE CHARACTERISTICS:
  (A) LENGTH: 894 base pairs
  (B) TYPE: nucleic acid
  (C) STRANDEDNESS: double
  (D) TOPOLOGY: linear (ii) MOLECULE TYPE: DNA (vi) ORIGINAL SOURCE:
  (A) ORGANISM: Bacillus stearothermophilus (xi) SEQUENCE DESCRIPTION: SEQ ID NO:3:

```
ATGGCGCAGC TTTCAGTTGA ACAGTTTCTC AACGAGCAAA AACAGGCGGT GGAAACAGCG    60
CTCTCCCGTT ATATAGAGCG CTTAGAAGGG CCGGCGAAGC TGAAAAAGGC GATGGCGTAC   120
TCATTGGAGG CCGGCGGCAA ACGAATCCGT CCGTTGCTGC TTCTGTCCAC CGTTCGGGCG   180
CTCGGAAAAG ACCCGGCGGT CGGATTGCCC GTCGCCTGCG CGATTGAAAT GATCCATACG   240
TACTCTTTGA TCCATGATGA TTTGCCGAGC ATGGACAACG ATGATTTGCG GCGCGGCAAG   300
CCGACGAACC ATAAAGTGTT CGGCGAGGCG ATGGCCATCT TGGCGGGGGA CGGGTTGTTG   360
ACGTACGCGT TTCAATTGAT CACCGAAATC GACGATGAGC GCATCCCTCC TTCCGTCCGG   420
CTTCGGCTCA TCGAACGGCT GGCGAAAGCG GCCGGTCCGG AAGGGATGGC CGCCGGTCAG   480
GCAGCCGATA TGGAAGGAGA GGGGAAAACG CTGACGCTTT CGGAGCTCGA ATACATTCAT   540
CGGTATAAAA CCGGGAAAAT GCTGCAATAC AGCGTGCACG CCGGCGCCTT GATCGGCGGC   600
GCTGATGCCC GGCAAACGCG GGAGCTTGAC GAATTCGCCG CCCATCTAGG CCTTGCCTTT   660
CAAATTCGCG ATGATATTCT CGATATTGAA GGGGCAGAAG AAAAAATCGG CAAGCCGGTC   720
GGCAGCGACC AAAGCAACAA CAAAGCGACG TATCCAGCGT TGCTGTCGCT TGCCGGCGCA   780
AAGGAAAAGT TGGCGTTCCA TATCGAGGCG GCGCAGCGCC ATTTACGGAA CGCCGACGTT   840
GACGGCGCCG CGCTCGCCTA TATTTGCGAA CTGGTCGCCG CCCGCGACCA TTAA         894
```

( 2 ) INFORMATION FOR SEQ ID NO:4:

( i ) SEQUENCE CHARACTERISTICS:
        ( A ) LENGTH: 894 base pairs
        ( B ) TYPE: nucleic acid
        ( C ) STRANDEDNESS: double
        ( D ) TOPOLOGY: linear ( i i ) MOLECULE TYPE: DNA ( v i ) ORIGINAL SOURCE:
        ( A ) ORGANISM: Bacillus stearothermophilus ( x i ) SEQUENCE DESCRIPTION: SEQ ID NO:4:

| | | | | | | |
|---|---|---|---|---|---|---|
| ATGGCGCAGC | TTTCAGTTGA | ACAGTTTCTC | AACGAGCAAA | AACAGGCGGT | GGAAACAGCG | 60 |
| CTCTCCCGTT | ATATAGAGCG | CTTAGAAGGG | CCGGCGAAGC | TGAAAAAGGC | GATGGCGTAC | 120 |
| TCATTGGAGG | CCGGCGGCAA | ACGAATCCGT | CCGTTGCTGC | TTCTGTCCAC | CGTTCGGGCG | 180 |
| CTCGGCAAAG | ACCCGGCGGT | CGGATTGCCC | GTCGCCTGCG | CGATTGAAAT | GATCCATACG | 240 |
| CACTCTTTGA | TCCATGATGA | TTTGCCGAGC | ATGGACAACG | ATGATTTGCG | GCGCGGCAAG | 300 |
| CCGACGAACC | ATAAAGTGTT | CGGCGAGGCG | ATGGCCATCT | TGGCGGGGA | CGGGTTGTTG | 360 |
| ACGTACGCGT | TTCAATTGAT | CACCGAAATC | GACGATGAGC | GCATCCCTCC | TTCCGTCCGG | 420 |
| CTTCGGCTCA | TCGAACGGCT | GGCGAAAGCG | GCCGGTCCGG | AAGGGATGGT | CGCCGGTCAG | 480 |
| GCAGCCGATA | TGGAAGGAGA | GGGGAAAACG | CTGACGCTTT | CGGAGCTCGA | ATACATTCAT | 540 |
| CGGCATAAAA | CCGGGAAAAT | GCTGCAATAC | AGCGTGCACG | CCGGCGCCTT | GATCGGCGGC | 600 |
| GCTGATGCCC | GGCAAACGCG | GGAGCTTGAC | GAATTCGCCG | CCCATCTAGG | CCTTGCCTTT | 660 |
| CAAATTCGCG | ATGATATTCT | CGATATTGAA | GGGGCAGAAG | AAAAAATCGG | CAAGCGGGTC | 720 |
| GGCAGCGACC | AAAGCAACAA | CAAAGCGACG | TATCCAGCGT | TGCTGTCGCT | TGCCGGCGCG | 780 |
| AAGGAAAAGT | TGACGTTCCA | TATCGAGGCG | GCGCAGCGCC | ATTTACGGAA | CGCCGACGTT | 840 |
| GACGGCGCCG | CGCTCGCCTA | TATTTGCGAA | CTGGTCGCCG | CCCGCGACCA | TTAA | 894 |

( 2 ) INFORMATION FOR SEQ ID NO:5:

( i ) SEQUENCE CHARACTERISTICS:
        ( A ) LENGTH: 894 base pairs
        ( B ) TYPE: nucleic acid
        ( C ) STRANDEDNESS: double
        ( D ) TOPOLOGY: linear ( i i ) MOLECULE TYPE: DNA ( v i ) ORIGINAL SOURCE:
        ( A ) ORGANISM: Bacillus stearothermophilus ( x i ) SEQUENCE DESCRIPTION: SEQ ID NO:5:

| | | | | | | |
|---|---|---|---|---|---|---|
| ATGGCGCAGC | TTTCAGTTGA | ACAGTTTCTC | AACGAGCAAA | AACAGGCGGT | GGAAACAGCG | 60 |
| CTCTCCCGTT | ATATAGAGCG | CTTAGAAGGG | CCGGCGAAGC | TGAAAAAGGC | GATGGCGTAC | 120 |
| TCATTGGAGG | CCGGCGGCAA | ACGAATCCGT | CCGTTGCTGC | TTCTGTCCAC | CGTTCAGGCG | 180 |
| CTCGGCAAAG | ACCCGGCGGT | CGGATTGCCC | GTCGCCTGCG | CGATTGAAAT | GATCCATACG | 240 |
| TACTCTTTGA | TCCATGATGA | TTTGCCGAGC | ATGGACAACG | ATGATTTGCG | GCGCGGCAAG | 300 |
| CCGACGAACC | ATAAAGTGTT | CGGCGAGGCG | ATGGCCATCT | TGGCGGGGA | CGGGTTGTTG | 360 |
| ACGTACGCGT | TTCAATTGAT | CACCGAAATC | GACGATGAGC | GCATCCCTCC | TTCCGTCCGG | 420 |
| CTTCGGCTCA | TCGAACGGCT | GGCGAAAGCG | GCCGGTCCGG | AAGGGATGGT | CGCCGGTCAG | 480 |
| GCAGCCGATA | TGGAAGGAGA | GGGGAAAACG | CTGACGCTTT | CGGAGCTCGA | ATACATTCAT | 540 |

-continued

```
CGGCATAAAA CCGGGAAAAT GCTGCAATAC AGCGTGCACG CCGGCGCCTT GATCGGCGGC      600

GCTGATGCCC GGCAAACGCG GGAGCTTGAC GAATTCGCCG CCCATCTAGG CCTTGCCTTT      660

CAAATTCGCG ATGATATTCT CGATATTGAA GGGGCAGAAG AAAAAATCGG CAAGCCGGTC      720

GGCAGCGACC AAAGCAACAA CAAAGCGACG TATCCAGCGT TGCTGTCGCT TGCCGGCGCG      780

AAGGAAAAGT TGGCGTTCCA TATCGAGGCG GCGCAGCGCC ATTTACGGAA CGCCGACGTT      840

GACGGCGCCG CGCTCGCCTA TATTTGCGAA CTGGTCGCCG CCCGCGACCA TTAA            894
```

( 2 ) INFORMATION FOR SEQ ID NO:6:

( i ) SEQUENCE CHARACTERISTICS:
        ( A ) LENGTH: 297 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Bacillus stearothermophilus ( x i ) SEQUENCE DESCRIPTION: SEQ ID NO:6:

```
Met Ala Gln Leu Ser Val Glu Gln Phe Leu Asn Glu Gln Lys Gln Ala
                  5                  10                  15

Val Glu Thr Ala Leu Ser Arg Tyr Ile Glu Arg Leu Glu Gly Pro Ala
             20                  25                  30

Lys Leu Lys Lys Ala Met Ala Tyr Ser Leu Glu Ala Gly Gly Lys Arg
         35                  40                  45

Ile Arg Pro Leu Leu Leu Leu Ser Thr Val Arg Ala Leu Gly Lys Asp
     50                  55                  60

Pro Ala Val Gly Leu Pro Val Ala Cys Ala Ile Glu Met Ile His Thr
 65                  70                  75                  80

His Ser Leu Ile His Asp Asp Leu Pro Ser Met Asp Asn Asp Asp Leu
                 85                  90                  95

Arg Arg Gly Lys Pro Thr Asn His Lys Val Phe Gly Glu Ala Met Ala
                100                 105                 110

Ile Leu Ala Gly Asp Gly Leu Leu Thr Tyr Ala Phe Gln Leu Ile Thr
            115                 120                 125

Glu Ile Asp Asp Glu Arg Ile Pro Pro Ser Val Arg Leu Arg Leu Ile
        130                 135                 140

Glu Arg Leu Ala Lys Ala Ala Gly Pro Glu Gly Met Val Ala Gly Gln
145                 150                 155                 160

Ala Ala Asp Met Glu Gly Glu Gly Lys Thr Leu Thr Leu Ser Glu Leu
                165                 170                 175

Glu Tyr Ile His Arg His Lys Thr Gly Lys Met Leu Gln Tyr Ser Val
            180                 185                 190

His Ala Gly Ala Leu Ile Gly Gly Ala Asp Ala Arg Gln Thr Arg Glu
        195                 200                 205

Leu Asp Glu Phe Ala Ala His Leu Gly Leu Ala Phe Gln Ile Arg Asp
    210                 215                 220

Asp Ile Leu Asp Ile Glu Gly Ala Glu Glu Lys Ile Gly Lys Pro Val
225                 230                 235                 240

Gly Ser Asp Gln Ser Asn Asn Lys Ala Thr Tyr Pro Ala Leu Leu Ser
                245                 250                 255

Leu Ala Gly Ala Lys Glu Lys Leu Ala Phe His Ile Glu Ala Ala Gln
            260                 265                 270

Arg His Ser Arg Asn Ala Asp Val Asp Gly Ala Ala Leu Ala Tyr Ile
```

| | | | 275 | | | | 280 | | | | 285 | | |
|---|---|---|---|---|---|---|---|---|---|---|---|---|---|
Cys Glu Leu Val Ala Ala Arg Asp His
290                     295

( 2 ) INFORMATION FOR SEQ ID NO:7:

( i ) SEQUENCE CHARACTERISTICS:
        ( A ) LENGTH: 297 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Bacillus stearothermophilus ( x i ) SEQUENCE DESCRIPTION: SEQ ID NO:7:

Met Ala Gln Leu Ser Val Glu Gln Phe Leu Asn Glu Gln Lys Gln Ala
                  5                  10                  15

Val Glu Thr Ala Leu Ser Arg Tyr Ile Glu Arg Leu Glu Gly Pro Ala
             20                  25                  30

Lys Val Lys Lys Ala Met Ala Tyr Ser Leu Glu Ala Gly Gly Lys Arg
         35                  40                  45

Ile Arg Pro Leu Leu Leu Leu Ser Thr Val Gln Ala Leu Gly Lys Asp
    50                  55                  60

Pro Ala Val Gly Leu Pro Val Ala Cys Ala Ile Glu Met Ile His Thr
65                  70                  75                  80

Tyr Ser Leu Ile His Asp Asp Leu Pro Ser Met Asp Asn Asp Asp Leu
                  85                  90                  95

Arg Arg Gly Lys Pro Thr Asn His Lys Val Phe Gly Glu Ala Met Ala
                 100                 105                 110

Ile Leu Ala Gly Asp Gly Leu Leu Thr Tyr Ala Phe Gln Leu Ile Thr
             115                 120                 125

Glu Ile Asp Asp Glu Arg Ile Pro Pro Ser Val Arg Leu Arg Leu Ile
    130                 135                 140

Glu Arg Leu Ala Lys Ala Ala Gly Pro Glu Gly Met Val Ala Gly Gln
145                 150                 155                 160

Ala Ala Asp Met Glu Gly Glu Gly Lys Thr Leu Thr Leu Ser Glu Leu
                 165                 170                 175

Glu Tyr Ile His Arg His Lys Thr Gly Lys Met Leu Gln Tyr Ser Val
             180                 185                 190

His Ala Gly Ala Leu Ile Gly Gly Ala Asp Ala Arg Gln Thr Arg Glu
    195                 200                 205

Leu Asp Glu Phe Ala Ala His Leu Gly Leu Ala Phe Gln Ile Arg Asp
    210                 215                 220

Asp Ile Leu Asp Ile Glu Gly Ala Glu Glu Lys Ile Gly Lys Pro Val
225                 230                 235                 240

Gly Ser Asp Gln Ser Asn Asn Lys Ala Thr Tyr Pro Ala Leu Leu Ser
                 245                 250                 255

Leu Ala Gly Ala Lys Glu Lys Leu Ala Phe His Ile Glu Ala Ala Gln
             260                 265                 270

Arg His Leu Arg Asn Ala Asp Val Asp Gly Ala Ala Leu Ala Tyr Ile
    275                 280                 285

Cys Glu Leu Val Ala Ala Arg Asp His
290                 295

( 2 ) INFORMATION FOR SEQ ID NO:8:

( i ) SEQUENCE CHARACTERISTICS:
    ( A ) LENGTH: 297 amino acids
    ( B ) TYPE: amino acid
    ( D ) TOPOLOGY: linear ( i i ) MOLECULE TYPE: protein ( v i ) ORIGINAL SOURCE:
    ( A ) ORGANISM: Bacillus stearothermophilus ( x i ) SEQUENCE DESCRIPTION: SEQ ID NO:8:

```
Met Ala Gln Leu Ser Val Glu Gln Phe Leu Asn Glu Gln Lys Gln Ala
                  5                  10                 15
Val Glu Thr Ala Leu Ser Arg Tyr Ile Glu Arg Leu Glu Gly Pro Ala
             20                  25                 30
Lys Leu Lys Lys Ala Met Ala Tyr Ser Leu Glu Ala Gly Gly Lys Arg
          35                  40                 45
Ile Arg Pro Leu Leu Leu Leu Ser Thr Val Arg Ala Leu Gly Lys Asp
       50                  55                 60
Pro Ala Val Gly Leu Pro Val Ala Cys Ala Ile Glu Met Ile His Thr
65                  70                  75                 80
Tyr Ser Leu Ile His Asp Asp Leu Pro Ser Met Asp Asn Asp Asp Leu
                  85                  90                 95
Arg Arg Gly Lys Pro Thr Asn His Lys Val Phe Gly Glu Ala Met Ala
              100                 105                110
Ile Leu Ala Gly Asp Gly Leu Leu Thr Tyr Ala Phe Gln Leu Ile Thr
          115                 120                125
Glu Ile Asp Asp Glu Arg Ile Pro Pro Ser Val Arg Leu Arg Leu Ile
       130                 135                140
Glu Arg Leu Ala Lys Ala Ala Gly Pro Glu Gly Met Ala Ala Gly Gln
145                 150                 155                160
Ala Ala Asp Met Glu Gly Glu Gly Lys Thr Leu Thr Leu Ser Glu Leu
              165                 170                175
Glu Tyr Ile His Arg Tyr Lys Thr Gly Lys Met Leu Gln Tyr Ser Val
          180                 185                190
His Ala Gly Ala Leu Ile Gly Gly Ala Asp Ala Arg Gln Thr Arg Glu
       195                 200                205
Leu Asp Glu Phe Ala Ala His Leu Gly Leu Ala Phe Gln Ile Arg Asp
    210                 215                220
Asp Ile Leu Asp Ile Glu Gly Ala Glu Glu Lys Ile Gly Lys Pro Val
225                 230                 235                240
Gly Ser Asp Gln Ser Asn Asn Lys Ala Thr Tyr Pro Ala Leu Leu Ser
              245                 250                255
Leu Ala Gly Ala Lys Glu Lys Leu Ala Phe His Ile Glu Ala Ala Gln
          260                 265                270
Arg His Leu Arg Asn Ala Asp Val Asp Gly Ala Ala Leu Ala Tyr Ile
       275                 280                285
Cys Glu Leu Val Ala Ala Arg Asp His
    290                 295
```

( 2 ) INFORMATION FOR SEQ ID NO:9:

( i ) SEQUENCE CHARACTERISTICS:
        ( A ) LENGTH: 297 amino acids
        ( B ) TYPE: amino acid
        ( D ) TOPOLOGY: linear ( i i ) MOLECULE TYPE: protein ( v i ) ORIGINAL SOURCE:

( A ) ORGANISM: Bacillus stearothermophilus ( x i ) SEQUENCE DESCRIPTION: SEQ ID NO:9:

| Met | Ala | Gln | Leu | Ser | Val | Glu | Gln | Phe | Leu | Asn | Glu | Gln | Lys | Gln | Ala |
|---|---|---|---|---|---|---|---|---|---|---|---|---|---|---|---|
| | | | | 5 | | | | | 10 | | | | | 15 | |

| Val | Glu | Thr | Ala | Leu | Ser | Arg | Tyr | Ile | Glu | Arg | Leu | Glu | Gly | Pro | Ala |
|---|---|---|---|---|---|---|---|---|---|---|---|---|---|---|---|
| | | | 20 | | | | | 25 | | | | | 30 | | |

| Lys | Leu | Lys | Lys | Ala | Met | Ala | Tyr | Ser | Leu | Glu | Ala | Gly | Gly | Lys | Arg |
|---|---|---|---|---|---|---|---|---|---|---|---|---|---|---|---|
| | | | 35 | | | | | 40 | | | | | 45 | | |

| Ile | Arg | Pro | Leu | Leu | Leu | Leu | Ser | Thr | Val | Arg | Ala | Leu | Gly | Lys | Asp |
|---|---|---|---|---|---|---|---|---|---|---|---|---|---|---|---|
| | 50 | | | | | 55 | | | | | 60 | | | | |

| Pro | Ala | Val | Gly | Leu | Pro | Val | Ala | Cys | Ala | Ile | Glu | Met | Ile | His | Thr |
|---|---|---|---|---|---|---|---|---|---|---|---|---|---|---|---|
| 65 | | | | | 70 | | | | | 75 | | | | | 80 |

| His | Ser | Leu | Ile | His | Asp | Asp | Leu | Pro | Ser | Met | Asp | Asn | Asp | Asp | Leu |
|---|---|---|---|---|---|---|---|---|---|---|---|---|---|---|---|
| | | | | 85 | | | | | 90 | | | | | 95 | |

| Arg | Arg | Gly | Lys | Pro | Thr | Asn | His | Lys | Val | Phe | Gly | Glu | Ala | Met | Ala |
|---|---|---|---|---|---|---|---|---|---|---|---|---|---|---|---|
| | | | | 100 | | | | | 105 | | | | | 110 | |

| Ile | Leu | Ala | Gly | Asp | Gly | Leu | Leu | Thr | Tyr | Ala | Phe | Gln | Leu | Ile | Thr |
|---|---|---|---|---|---|---|---|---|---|---|---|---|---|---|---|
| | | | 115 | | | | | 120 | | | | | 125 | | |

| Glu | Ile | Asp | Asp | Glu | Arg | Ile | Pro | Pro | Ser | Val | Arg | Leu | Arg | Leu | Ile |
|---|---|---|---|---|---|---|---|---|---|---|---|---|---|---|---|
| | 130 | | | | | 135 | | | | | 140 | | | | |

| Glu | Arg | Leu | Ala | Lys | Ala | Ala | Gly | Pro | Glu | Gly | Met | Val | Ala | Gly | Gln |
|---|---|---|---|---|---|---|---|---|---|---|---|---|---|---|---|
| 145 | | | | | 150 | | | | | 155 | | | | | 160 |

| Ala | Ala | Asp | Met | Glu | Gly | Glu | Gly | Lys | Thr | Leu | Thr | Leu | Ser | Glu | Leu |
|---|---|---|---|---|---|---|---|---|---|---|---|---|---|---|---|
| | | | | 165 | | | | | 170 | | | | | 175 | |

| Glu | Tyr | Ile | His | Arg | His | Lys | Thr | Gly | Lys | Met | Leu | Gln | Tyr | Ser | Val |
|---|---|---|---|---|---|---|---|---|---|---|---|---|---|---|---|
| | | | 180 | | | | | 185 | | | | | 190 | | |

| His | Ala | Gly | Ala | Leu | Ile | Gly | Gly | Ala | Asp | Ala | Arg | Gln | Thr | Arg | Glu |
|---|---|---|---|---|---|---|---|---|---|---|---|---|---|---|---|
| | | 195 | | | | | 200 | | | | | 205 | | | |

| Leu | Asp | Glu | Phe | Ala | Ala | His | Leu | Gly | Leu | Ala | Phe | Gln | Ile | Arg | Asp |
|---|---|---|---|---|---|---|---|---|---|---|---|---|---|---|---|
| | 210 | | | | | 215 | | | | | 220 | | | | |

| Asp | Ile | Leu | Asp | Ile | Glu | Gly | Ala | Glu | Glu | Lys | Ile | Gly | Lys | Arg | Val |
|---|---|---|---|---|---|---|---|---|---|---|---|---|---|---|---|
| 225 | | | | | 230 | | | | | 235 | | | | | 240 |

| Gly | Ser | Asp | Gln | Ser | Asn | Asn | Lys | Ala | Thr | Tyr | Pro | Ala | Leu | Leu | Ser |
|---|---|---|---|---|---|---|---|---|---|---|---|---|---|---|---|
| | | | | 245 | | | | | 250 | | | | | 255 | |

| Leu | Ala | Gly | Ala | Lys | Glu | Lys | Leu | Thr | Phe | His | Ile | Glu | Ala | Ala | Gln |
|---|---|---|---|---|---|---|---|---|---|---|---|---|---|---|---|
| | | | 260 | | | | | 265 | | | | | 270 | | |

| Arg | His | Leu | Arg | Asn | Ala | Asp | Val | Asp | Gly | Ala | Ala | Leu | Ala | Tyr | Ile |
|---|---|---|---|---|---|---|---|---|---|---|---|---|---|---|---|
| | | 275 | | | | | 280 | | | | | 285 | | | |

| Cys | Glu | Leu | Val | Ala | Ala | Arg | Asp | His |
|---|---|---|---|---|---|---|---|---|
| 290 | | | | | 295 | | | |

( 2 ) INFORMATION FOR SEQ ID NO:10:

( i ) SEQUENCE CHARACTERISTICS:
  ( A ) LENGTH: 297 amino acids
  ( B ) TYPE: amino acid
  ( D ) TOPOLOGY: linear ( i i ) MOLECULE TYPE: protein ( v i ) ORIGINAL SOURCE:
  ( A ) ORGANISM: Bacillus stearothermophilus ( x i ) SEQUENCE DESCRIPTION: SEQ ID NO:10:

| Met | Ala | Gln | Leu | Ser | Val | Glu | Gln | Phe | Leu | Asn | Glu | Gln | Lys | Gln | Ala |
|---|---|---|---|---|---|---|---|---|---|---|---|---|---|---|---|
| | | | | 5 | | | | | 10 | | | | | 15 | |

| Val | Glu | Thr | Ala | Leu | Ser | Arg | Tyr | Ile | Glu | Arg | Leu | Glu | Gly | Pro | Ala |

-continued

```
                    20                          25                              30
Lys  Lys  Lys  Lys  Ala  Met  Ala  Tyr  Ser  Leu  Glu  Ala  Gly  Gly  Lys  Arg
          35                        40                          45

Ile  Arg  Pro  Leu  Leu  Leu  Leu  Ser  Thr  Val  Gln  Ala  Leu  Gly  Lys  Asp
     50                        55                      60

Pro  Ala  Val  Gly  Leu  Pro  Val  Ala  Cys  Ala  Ile  Glu  Met  Ile  His  Thr
65                        70                      75                          80

Tyr  Ser  Leu  Ile  His  Asp  Asp  Leu  Pro  Ser  Met  Asp  Asn  Asp  Asp  Leu
                    85                        90                        95

Arg  Arg  Gly  Lys  Pro  Thr  Asn  His  Lys  Val  Phe  Gly  Glu  Ala  Met  Ala
               100                      105                      110

Ile  Leu  Ala  Gly  Asp  Gly  Leu  Leu  Thr  Tyr  Ala  Phe  Gln  Leu  Ile  Thr
          115                      120                      125

Glu  Ile  Asp  Asp  Glu  Arg  Ile  Pro  Pro  Ser  Val  Arg  Leu  Arg  Leu  Ile
     130                      135                      140

Glu  Arg  Leu  Ala  Lys  Ala  Ala  Gly  Pro  Glu  Gly  Met  Val  Ala  Gly  Gln
145                      150                      155                           160

Ala  Ala  Asp  Met  Glu  Gly  Glu  Gly  Lys  Thr  Leu  Thr  Leu  Ser  Glu  Leu
               165                      170                          175

Glu  Tyr  Ile  His  Arg  His  Lys  Thr  Gly  Lys  Met  Leu  Gln  Tyr  Ser  Val
          180                      185                      190

His  Ala  Gly  Ala  Leu  Ile  Gly  Gly  Ala  Asp  Ala  Arg  Gln  Thr  Arg  Glu
          195                      200                      205

Leu  Asp  Glu  Phe  Ala  Ala  His  Leu  Gly  Leu  Ala  Phe  Gln  Ile  Arg  Asp
     210                      215                      220

Asp  Ile  Leu  Asp  Ile  Glu  Gly  Ala  Glu  Glu  Lys  Ile  Gly  Lys  Pro  Val
225                      230                      235                           240

Gly  Ser  Asp  Gln  Ser  Asn  Asn  Lys  Ala  Thr  Tyr  Pro  Ala  Leu  Leu  Ser
               245                      250                      255

Leu  Ala  Gly  Ala  Lys  Glu  Lys  Leu  Ala  Phe  His  Ile  Glu  Ala  Ala  Gln
               260                      265                      270

Arg  His  Leu  Arg  Asn  Ala  Asp  Val  Asp  Gly  Ala  Ala  Leu  Ala  Tyr  Ile
          275                      280                      285

Cys  Glu  Leu  Val  Ala  Ala  Arg  Asp  His
     290                      295
```

1

MUTATED FARNESYLDIPHOSHATE SYNTHASE CAPABLE OF SYNTHESIZING GERANYLGERANYLDIPHOSPHATE AND GENE CODING THEREFOR

BACKGROUND OF INVENTION

1. Field of Invention

The present invention relates to the mutated farnesyldiphosphate synthase capable of synthesizing geranylgeranyldiphosphate and a process for production thereof, as well as genes coding for said mutated enzymes and a process for isolation thereof.

2. Related Art

In nature there are various isoprenoid chain compounds comprising 5 carbon atom-basic structure, isoprene units, and these isoprenoid compounds play important roles for the life of various organisms. It is known that the chain-extension mechanism is catalyzed by a series of prenyltransferases which catalyze a series of catalytic reactions comprising sequential condensation of isopentenyldiphosphate (IPP) having 5 carbon atoms with its isomer dimethylallyldiphosphate (DMAPP). Among the isoprenoid compounds, farnesyldiphosphate (FPP) having 15 carbon atoms is positioned at a branching point in a biosynthesis pathway, from which various physiologically important start to geranylgeranyldiphosphate (GGPP) having 20 carbon atoms, to quinones, squalene, to steroids, farnesylated protein, dolichol etc.

Different prenyltransferases synthesize different isoprenoid compounds having different lengths. However, prenyltransferases have a common activity to condense an isoprenoid unit to extend the chain, and in fact, amino acids essential for the condensation are being clarified on the basis of homology of amino acid sequences of different prenyltransferases. However, the mechanism which determines the length of the isoprenoid compound have not yet clarified.

A biosynthesis pathway for geranyldiphosphate (GPP), farnesyldiphosphate (FPP) and geranylgeranyldiphosphate (GGPP) starting from an isoprenoid unit is shown in FIG. 1. In this biosynthesis pathway, the prenyltransferase which synthesizes farnesyldiphosphate is designated "farnesyldiphosphate synthase", and the prenyltransferase which synthesizes geranylgeranyldiphosphate is designated "geranylgeranyldiphosphate synthase". Farnesyldiphosphate synthases are known in *Bacillus thermophils* (J. Biochem. 113, 355–363 (1993)), *E. coli* (J. Biochem. 108, 995–1000 (1990)), yeast (J.B.C. 265, 19176–19184 (1989)), rats (Mol. Cell. Biol. 7, 3138–3146 (1987)) and in humans (J.B.C. 265, 4607–4616 (1990)), and their amino acid sequences are also known.

On the other hand, geranylgeranyldiphosphate synthases are known in *Rhodopseudomonas capusulata* (J. Bacteriol. 154, 580–590 (1983)), *Erwinia uredovora* (J. Bacteriol. 172, 6704–6712 (1990)), *Sulfolobus acidocaldarius* (J.B.C. 269, 14792–14797 (1994)) etc.

However, it had not been known that an enzyme having geranylgeranyldiphosphate synthase activity can be obtained by mutation of farnesyldiphosphate synthase.

SUMMARY OF INVENTION

Accordingly, the present invention provides a novel geranylgeranyldiphosphate synthase obtainable by mutating a farnesyldiphosphate synthase and a process for production thereof, as well as gene system therefor and a process for isolation of the gene.

2

More specifically, the present invention provides a process for production of a gene coding for geranylgeranyldiphosphate synthase comprising the steps of:

(1) subjecting genes coding for a farnesyldiphosphate synthase to a mutagenesis;

(2) expressing the genes subjected to the mutagenesis, and (3) selecting a gene which provides a geranylgeranyldiphosphate synthase.

The present invention further provides a gene coding for geranylgeranyldiphosphate synthase, an expression vector containing said gene, and a host transformed with said vector.

The present invention also provides a process for production of geranylgeranyldiphosphate synthase comprising expressing said gene, and geranylgeranyldiphosphate synthase obtainable by said process.

From another point of view, the present invention provides a geranylgeranyldiphosphate synthase having an amino acid sequence modified from an amino acid sequence of native farnesyldiphosphate synthase wherein the modification is deletion of one or more amino acids, addition of one or more amino acids, and/or replacement of one or more amino acids with other amino acids.

The present invention still further provides a gene coding for the above-mentioned geranylgeranyldiphosphate synthase, a vector, especially an expression vector comprising said gene, and a host transformed with said vector.

The present invention further provides a process for production of geranylgeranyldiphosphate synthase comprising the steps of cultivation said host, and purification the geranylgeranyldiphosphate synthase from the culture.

The present invention further provides a process for production of geranylgeranyldiphosphate or geranylgeranyol, comprising the steps of acting the present geranylgeranyldiphosphate synthase on isopentenyldiphosphate, dimethylallyldiphosphate, geranyldiphosphate or farnesyldiphosphate as a substrate.

BRIEF EXPLANATION OF DRAWINGS

FIG. 2 shows the homology of amino acid sequences of farnesyldiphosphate synthase derived from different species. In this Figure, the sequences in the boxes A to E show regions having relatively high homology and which are expected to participate in enzyme activity.

FIG. 3 shows the homology of amino acid sequences of farnesyldiphosphate synthase derived from different species. In this Figure, the sequences in the boxes F and G show regions having relatively high homology and which are expected to participate in enzyme activity.

FIG. 4 shows a native amino acid sequence of farnesyldiphosphate synthase derived from *Bacillus stearothermophilus* (indicated as W.T), and the mutated points in amino acid sequences of the modified enzymes having geranylgeranyldiphosphate synthase activity (No. 1 to No. 4).

DETAILED DESCRIPTION

Figure 1:
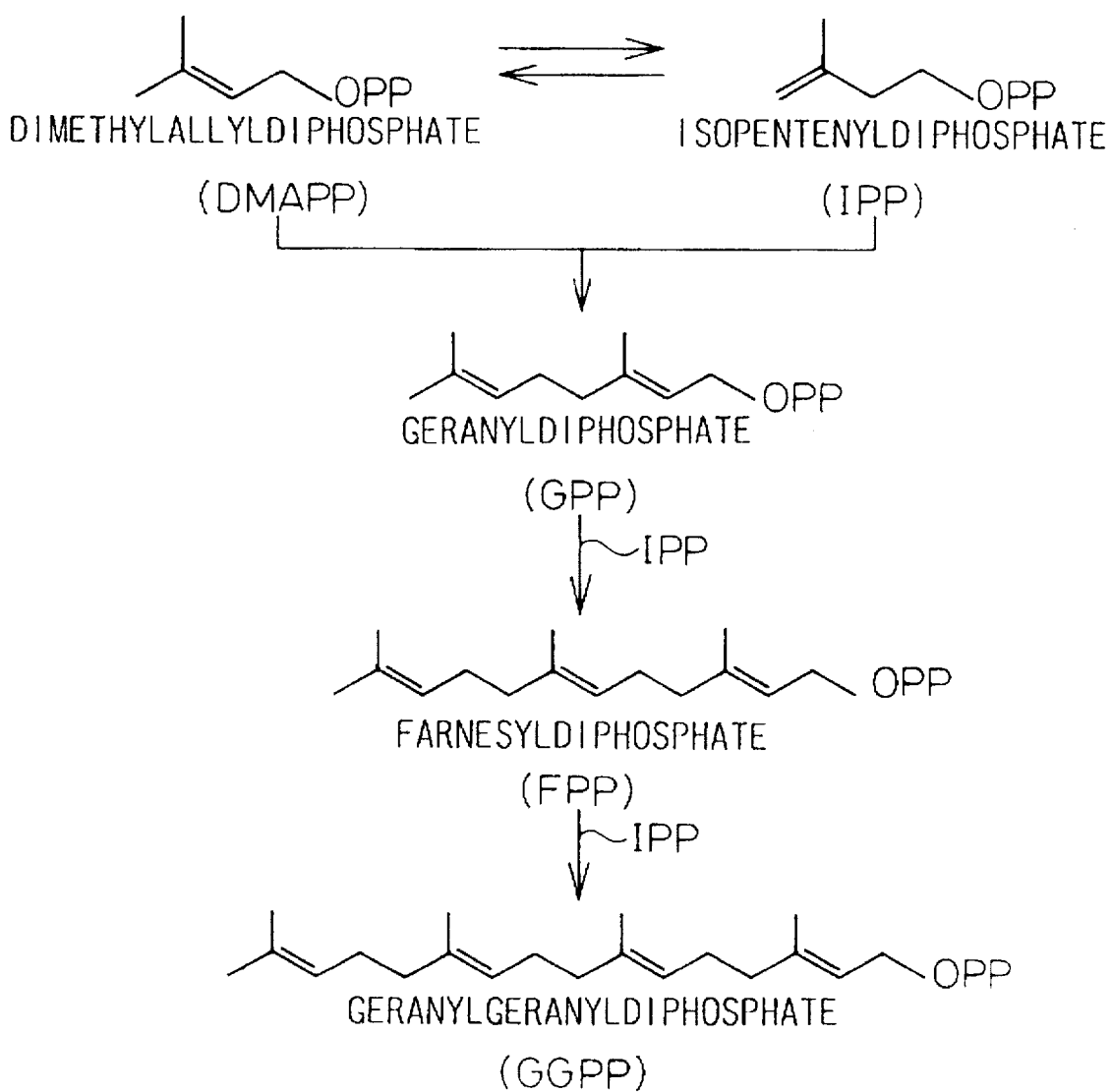
FIG. 1 represents a biosynthesis pathway for farnesyldiphosphate and geranylgeranyldiphosphate.

Genes of the present invention can be obtained by subjecting a gene coding for a farnesyldiphosphate synthase to mutagenesis, expressing the genes subjected to the mutagenesis, and selecting a gene providing a protein having geranylgeranyldiphosphate synthase activity.

Genes coding for a farnesyldiphosphate synthase used in the present invention may be those of any origin. For example, farnesyldiphosphate synthases of E. coli, yeast, human, rat etc., as well as genes coding therefor are known, and amino acid sequences of these enzymes have high homology as shown in FIG. 2. Therefore, in addition to the gene derived from Bacillus stearothermophilus as described in detail, according to the present invention, any gene coding for an amino acid sequence having a high homology, for example, at least 20% homology with the amino acid sequence of farnesyldiphosphate synthase derived from Bacillus stearothermophilus can be used regardless of its origin. As such gene sources, for example, Bacillus stearothermophilus, E. coli, yeast, humans, rats etc. can be used.

The gene to be mutated is an RNA or DNA coding for a farnesyldiphosphate synthase and sensitive to treatment with a mutagen, and DNA is preferably used for to ease of handling, and especially a single-stranded DNA is preferred due to its high mutation ratio.

A single-stranded DNA can be easily prepared according to a conventional procedure for preparing a single-stranded DNA, for example, by inserting a double-stranded DNA into a phage, introducing the phage into E. coli cells, culturing the E. coli cells and recovering the phage from the resulting lysate solution; or by introducing a desired double-stranded DNA into host cells, infecting the host cells with helper phage, culturing the host cells and recovering the phage from the resulting lysate solution.

Mutation of a gene can be carried out according to a conventional procedure for artificially mutating a gene. The mutation methods can be a physical method such as irradiation with X-rays, ultraviolet rays, etc., a chemical method such as treatment with a mutagen, a method of cis incorporation by DNA polymerase, a method using synthetic oligonucleotides etc. A chemical method is preferable for ease of operation and a high mutation ratio. As a mutagen, a nitrite, such as sodium nitrite, or the like can be used. To mutate a single-stranded DNA, a nitrite is preferable. Mutagenesis is preferably carried out at a nitrite concentration of 0.01 to 2M, for example, at about 0.1 to 1M, at a temperature of 20° to 30° C., for 10 to 120 minutes.

To select a gene coding for a protein having geranylgeranyldiphosphate synthase activity from the genes subjected to the mutagenesis, the gene subjected to the mutagenesis is inserted in an expression vector, the vector is introduced into host cells, the enzyme is expressed, and the expression product is tested for geranylgeranyldiphosphate synthase activity. Geranylgeranyldiphosphate is converted to phytoene by a phytoene synthase, and the phytoene is converted to lycopene having red color by a phytoene desaturase.

Accordingly, for example, a gene coding for a phytoene synthase and a gene coding for phytoene desaturase are inserted into an expression vector, the vector is introduced into host cells such as E. coli cells, and further an expression plasmid comprising a DNA to be tested is introduced into said host cells, and the double transformed host cells are cultured. If the gene to be tested encodes a geranylgeranyldiphosphate synthase, and the geranylgeranyldiphosphate produced by the gene expression is converted to phytoene and further to lycopene, the cells are red-colored. Accordingly, a desired gene can be selected very easily and efficiently by selecting a red-colored colony.

The present invention provides a protein having geranylgeranyldiphosphate synthase activity, i.e., a geranylgeranyldiphosphate synthase, having an amino acid sequence modified from a native amino acid sequence of a farnesyldiphosphate synthase. Here, the modification of an amino acid sequence means replacement of one or a few amino acids with other amino acids, deletion of one or a few amino acids or addition of one or a few amino acids, or a combination of these modifications. The amino acid replacement is especially preferable. Regarding the number of amino acids to be modified, "a few amino acids" means usually about 15 amino acids, preferably about 10 amino acids, and more preferably about 5 amino acids. Namely, according to the present invention, the number of mutated amino acids is about 1 to 15, preferably about 1 to 10, and more preferably 1 to 5.

To determine the positions of modified amino acids, after the mutagenesis and the selection of a gene coding for a geranylgeranyldiphosphate synthase, a nucleotide sequence of the selected gene is determined, and an amino acid sequence is predicted from the determined nucleotide sequence, the predicted amino acid sequence of the modified enzyme is composed with the corresponding native amino acid sequence. Amino acid sequences thus determined of the modified enzymes are shown in FIG. 4.

In FIG. 4, the row indicated by the symbol W.T shows, by the one-letter expression, a native amino acid sequence of farnesyldiphosphate synthase of Bacillus stearothermophilus origin, and the rows Nos. 1 to 4 show representative amino acid sequences which acquired geranylgeranyldiphosphate synthase activity by amino acid replacement in the amino acid sequence of the farnesyldiphosphate synthase, wherein only the amino acids different from the corresponding amino acids in the native amino acid sequence of the farnesyldiphosphate synthase shown in the line T.W are indicated by the one-letter expression of amino acid.

The modified enzyme No. 1 has two mutations, i.e., the 81st position (Tyr→His) and 275th position (Leu→Ser); the modified enzyme No. 2 has two mutations, i.e., 34th position (Leu-Val) and 59th position (Arg→Gln); the modified enzyme No. 3 has two mutations, i.e., 157th position (Val→Ala) and 182nd position (His→Tyr); and the modified enzyme No. 4 has three mutations, i.e., 81st position (Tyr→His), 238th position (Pro→Arg) and 265th position (Ala→Thr). The amino acid sequences No. 1 to 4 of the above-mentioned modified enzymes and nucleotide sequences coding therefor are shown in SEQ ID NO: 1 to 4, and the native amino acid sequence and a nucleotide sequence coding therefor is shown in SEQ ID NO: 5.

In the present invention, the amino acid sequence farnesyldiphosphate synthase of Bacillus stearothermophilus origin was used as a specific example. However, as shown in FIGS. 2 and 3, farnesyldiphosphate synthases have high homology among a wide spectrum of species covering those derived from the eukaryotes including humans and those derived from prokaryotes including bacteria. Therefore, the present invention can be applied to enzymes derived from various species to obtain novel geranylgeranyldiphosphate synthase.

As shown in FIG. 4, amino acid modification such as replacement occurs on the 34th, 59th, 81st, 157th, 182nd, 239th, 265th, and/or 275th positions of farnesyldiphosphate of *Bacillus stearothermophilus*. For enzymes from other species, it is expected that replacement at positions corresponding to the above-mentioned positions of the farnesyldiphosphate synthase of *Bacillus stearothermophilus* origin provides similar effects as that for the modified enzyme derived from *Bacillus stearothermophilus*. Therefore, the present invention can be applied to any farnesyldiphosphate synthases.

The present invention also relates to genes coding for the various geranylgeranyldiphosphate synthases derived from a farnesyldiphosphate synthase. These genes can be obtained by mutation of a gene coding for a corresponding native amino acid sequence. In addition, once the position of mutated amino acid is determined, a gene coding for the modified enzyme can be obtained by site-specific mutagenesis using a mutagenic primer. In addition, once an entire amino acid sequence is determined, a DNA coding for the amino acid sequence can be chemically synthesized according to a conventional procedure.

Genes coding for farnesyldiphosphate synthases used as starting materials to obtain the present genes have been cloned from various organisms, and therefore they can be used. For example, a gene of *Bacillus stearothermophilus* origin is described in J. Biochem. 113, 355–363 (1993), a gene of *E. coli* origin is described in J. Biochem. 108, 995–1000 (1990), a gene of yeast origin is described in J.B.C. 264, 19176–19184 (1989), a gene of rat origin is described in Mol. Cell. Biol. 7, 3138–3146 (1987), and a gene of human origin is described in J.B.C. 265, 4607–4614 (1990).

The present invention further provides recombinant vectors, especially expression vectors, comprising the above-mentioned gene (DNA), recombinant host transformed with said vector, and a process for production of said enzyme using said recombinant host.

As an example, where *E. coli* is used as a host, it is known that there are gene expression control mechanisms which regulate transcription of DNA to mRNA, translation of mRNA to protein etc.

As promoter sequences which control the synthesis of mRNA, naturally occurring sequences such as lac, trp, bla, lpp, PL, PR, tet, T3, T7 et al., as well as mutants thereof, such as lacUV5, sequences prepared by fusing naturally occurring promoter sequences, such as tac, tra, etc. are known, and they can be used in the present invention.

As sequences which control the ability to synthesize a protein from mRNA, it is known that a ribosome-binding site (GAGG and similar sequence) and the distance between the ribosome-binding site and the start codon ATG are important. In addition, it is known that a terminator which directs the termination of transcription at the 3'-end (for example, a vector comprising rrnBT1T2 is commercially available from Pharmacia) influences the efficiency of protein synthesis in a recombinant host.

As starting vectors to prepare recombinant vectors of the present invention, those commercially available can be used. Alternatively, various vectors derivatized according to a particular purpose can be used. For example, pBR322, pBR327, pKK223-2, pKK233-2, pTrc99A etc. containing a replicon derived from pMB1; pUC18, pUC19, pUC118, pUC119, pTV118N, pTV119N, pHSG298, pHSG396 etc., which have been modified to increase copy number; pACYC177, pACYC184 etc. containing a replicon derived from p15A; as well as plasmids derived from pSC101, C01E1, R1 or F-factor, may be mentioned.

Further, in addition to plasmids, viral vectors such as λ phage, M13 phage etc., and transposones can be used for introduction of a gene. These vectors are described in Molecular cloning (J. Sambrook, E. F. Fritsch, J. Maniatis, Cold Spring Harbor Laboratory Press); Cloning vector (P. H. Pouwels, B. E. Enger-Valk, W. J. Brammer, Elsevier); and catalogs of manufacturers of vectors.

Especially preferable is pTrc99 (commercially available for Pharmacia) which has an ampicillin resistance gene as a selective maker, Ptrc and lacI$^q$ as a promoter and control gene, an AGGA sequence as a ribosome-binding site and rrnBT1T2 as a terminator, and therefore has a function to control an expression of a geranylgeranyldiphosphate synthase.

Introduction of a DNA coding for geranylgeranyldiphosphate synthase and if necessary DNA fragments having a function to control the expression of said gene into the above-mentioned vectors can be carried out using appropriate restriction enzymes and ligases according to a conventional procedure.

Such a recombinant vector can be used to transform a microorganism such as *Escherichia coli*, Bacillus etc. Transformation can be carried out according to a conventional procedure, for example by the $CaCl_2$ method, protoplast method etc. described, for example, in Molecular cloning (J. Sambrook, E. F. Fritsch, T. Maniatis, Cold Spring Harbor Laboratory Press), DNA cloning Vol. I to III (D. M. Glover, IRLPRESS).

Although methods for expression of the present gene in *E. coli* was described in detail, according to the present invention, a DNA coding for a geranylgeranyldiphosphate synthase is inserted into a conventional expression vector according to a conventional procedure, and the vector is used to transform a host, for example, prokaryotic cells such as various bacterial cells, lower eukaryotic cells for example single cell hosts, for example, yeast cells, or higher eukaryotic cells such as silk-worm. After transformation, the transformant is cultured to produce a geranylgeranyldiphosphate synthase, according to a conventional process.

When a transformant host such as *E. coli* is cultured, geranylgeranyldiphosphate synthase is intracellularly accumulated. To recover the geranylgeranyldiphosphate from the cultured host cells, the cells are treated physiologically or chemically, for example, with a cell lysating agent to lyze the cells. The cell debris is removed, and the supernatant is subjected to an isolation process conventional for purification of enzymes. The above-mentioned cell-lysing enzyme is preferably lysozyme, and the physical treatment is preferably treatment with ultrasonic radiation. When the supernatant is heated to a temperature of about 55° C., proteins intrinsic to *E. coli* are insolubilized and removed as an insoluble precipitate. To purify the enzyme, gel-filtration chromatography, ion exchange chromatography, hydrophobic chromatography, reversed chromatography, and affinity chromatography can be used alone or in combination. During the purification and isolation steps, the desired enzyme can be stabilized by addition of a reducing agent such as dithiothreitol, protecting agent against proteases such as PMSF, BSA etc., metal ions such as magnesium, alone or in combination.

The present invention further provides a process for production of geranylgeranyldiphosphate or geranylgeranyol. In this process, isopentenyldiphosphate, dimethylallyldiphosphate, geranyldiphosphate, farnesyldiphosphate may be used as substrates.

EXAMPLES

Next, the present invention is explained in more detail by means of examples, though the present invention is not limited thereto.

Figure 5:
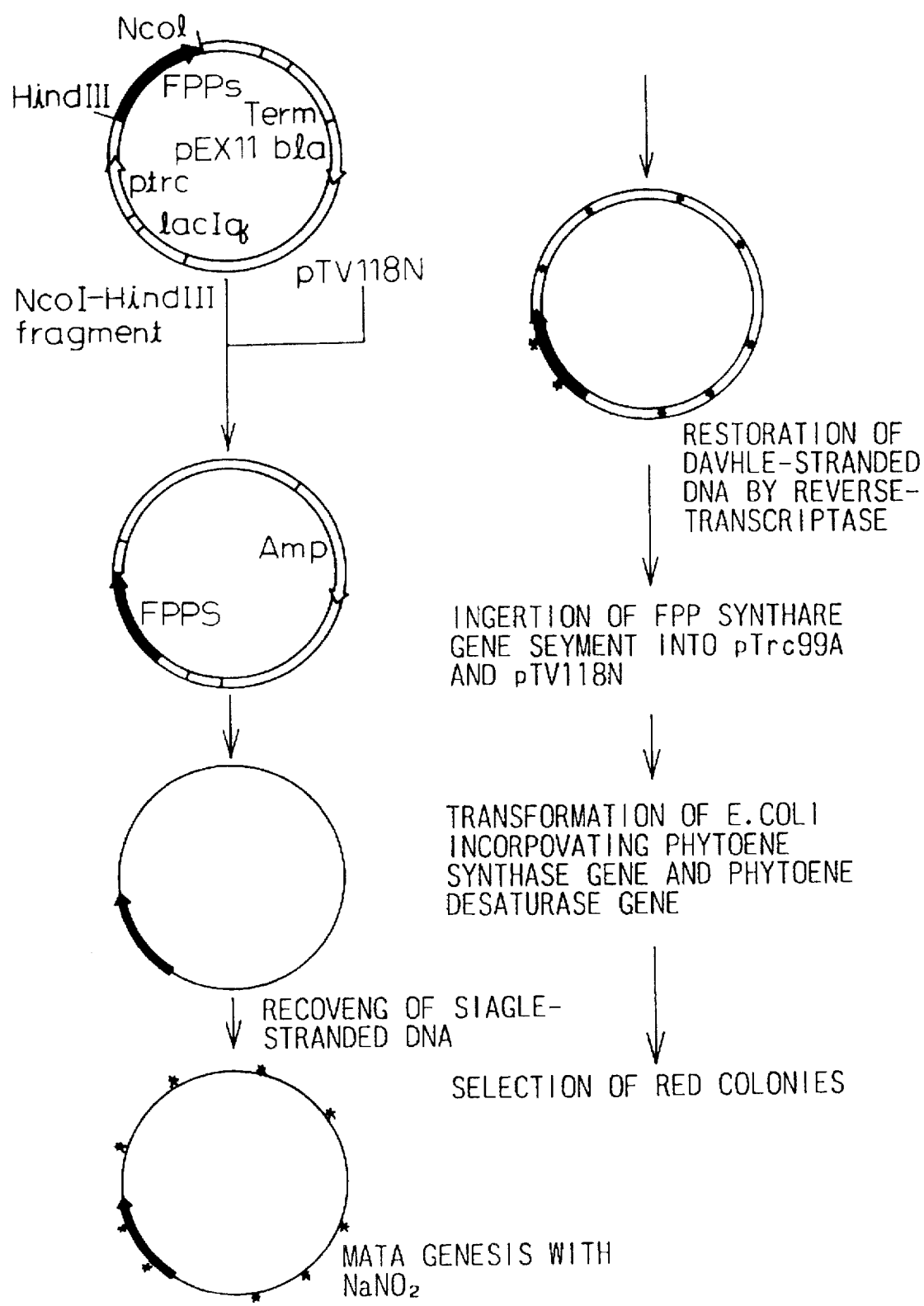
FIG. 5 schematically shows a process for construction of the present modified gene.
Figure 6:
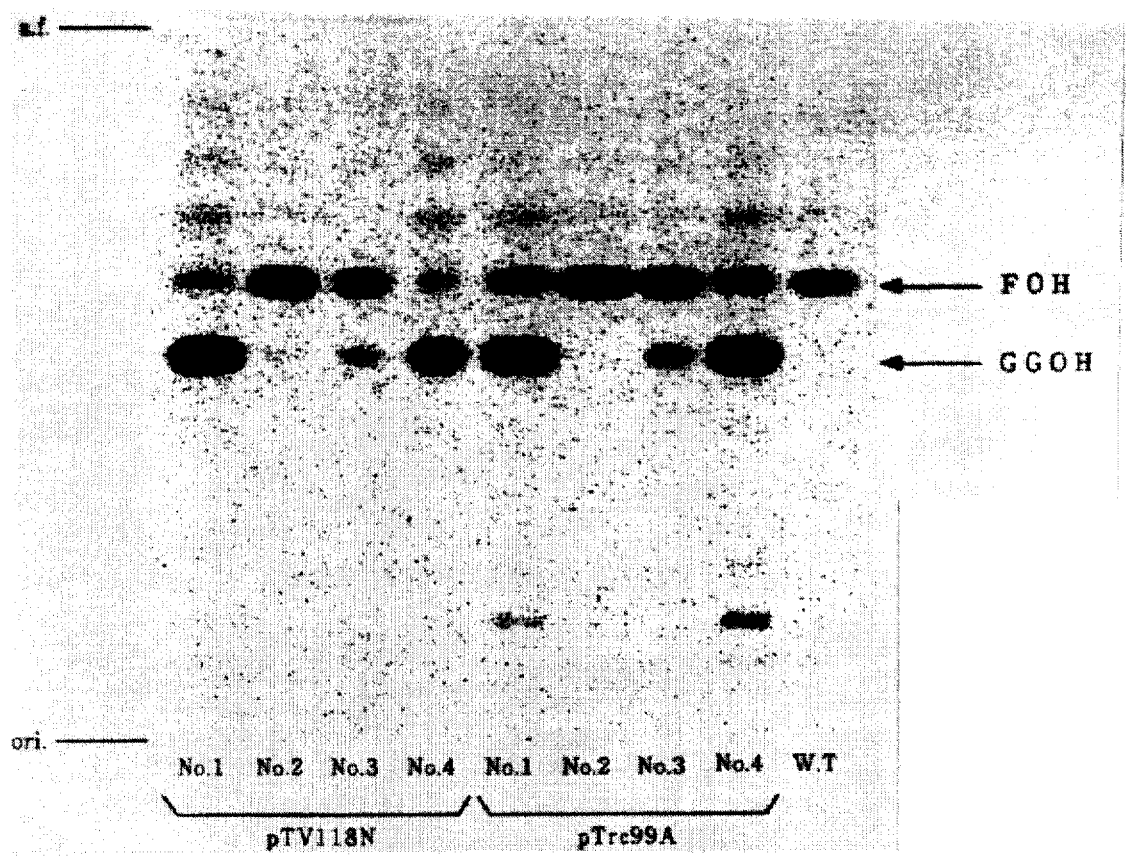
FIG. 6 is a profile of reversed phase TLC (developer: acetone/water=9/1) showing products formed by acting the present enzyme on a substrate dimethylallyldiphosphate.
Figure 7:
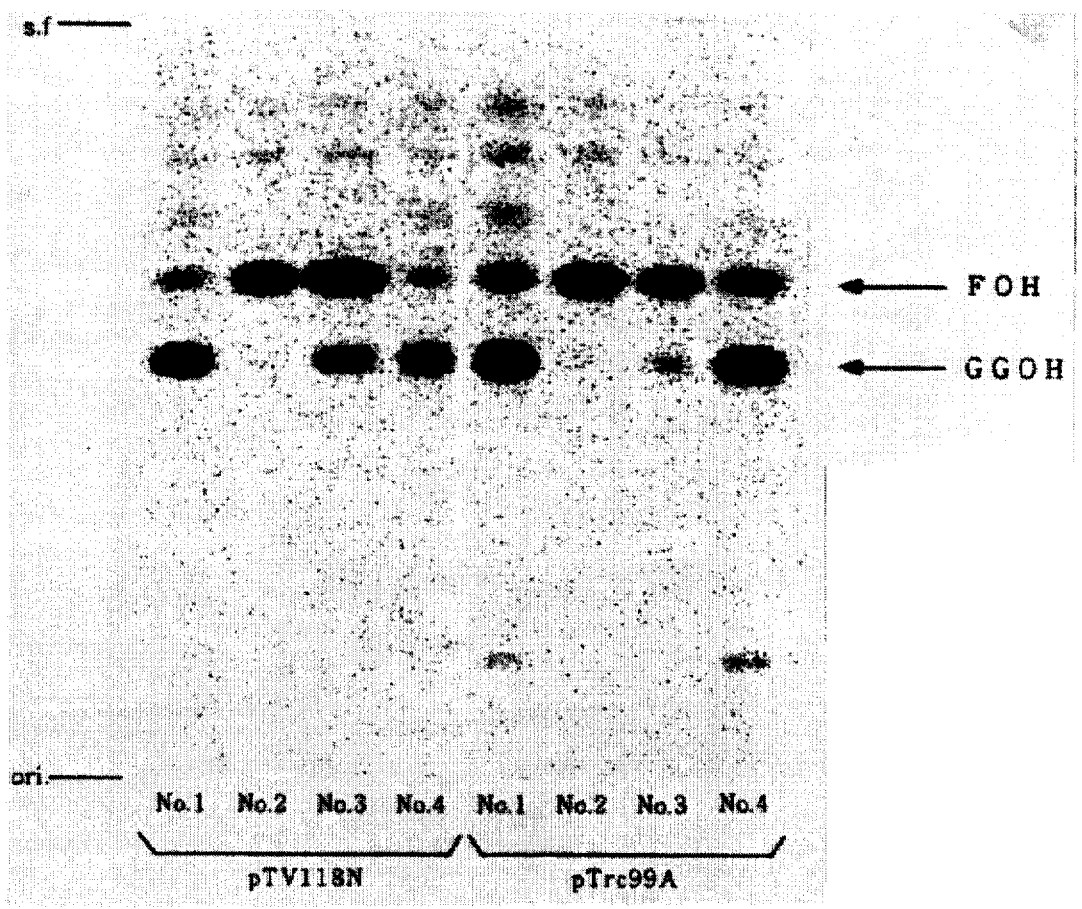
FIG. 7 is a profile of a reversed-phase TLC (developer: acetone/water=9/1) showing products formed by acting the present enzyme on a substrate geranyldiphosphate.
Figure 8:
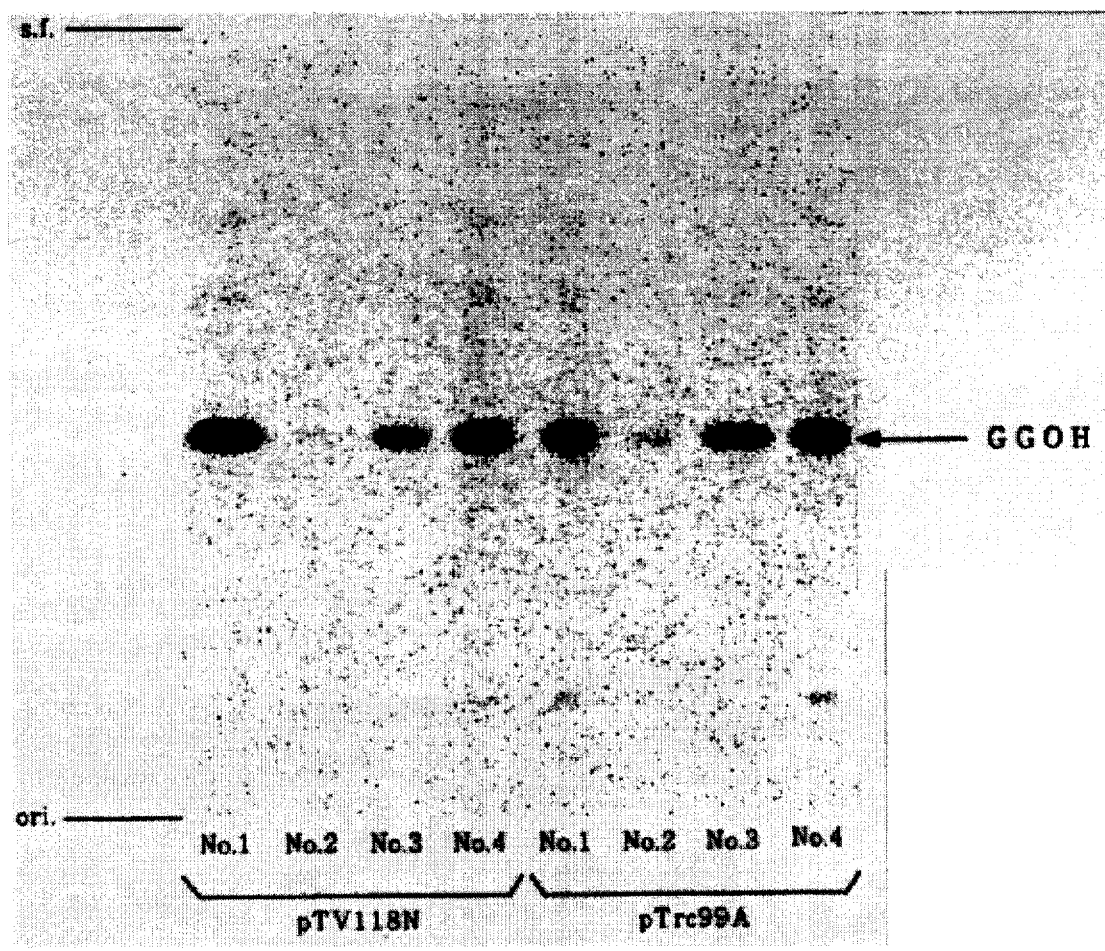
FIG. 8 is a profile of a reversed phase TLC (developer: acetone/water=9/1) showing products formed by acting the present enzyme on a substrate (all-E)-farnesyldiphosphate.
Figure 9:
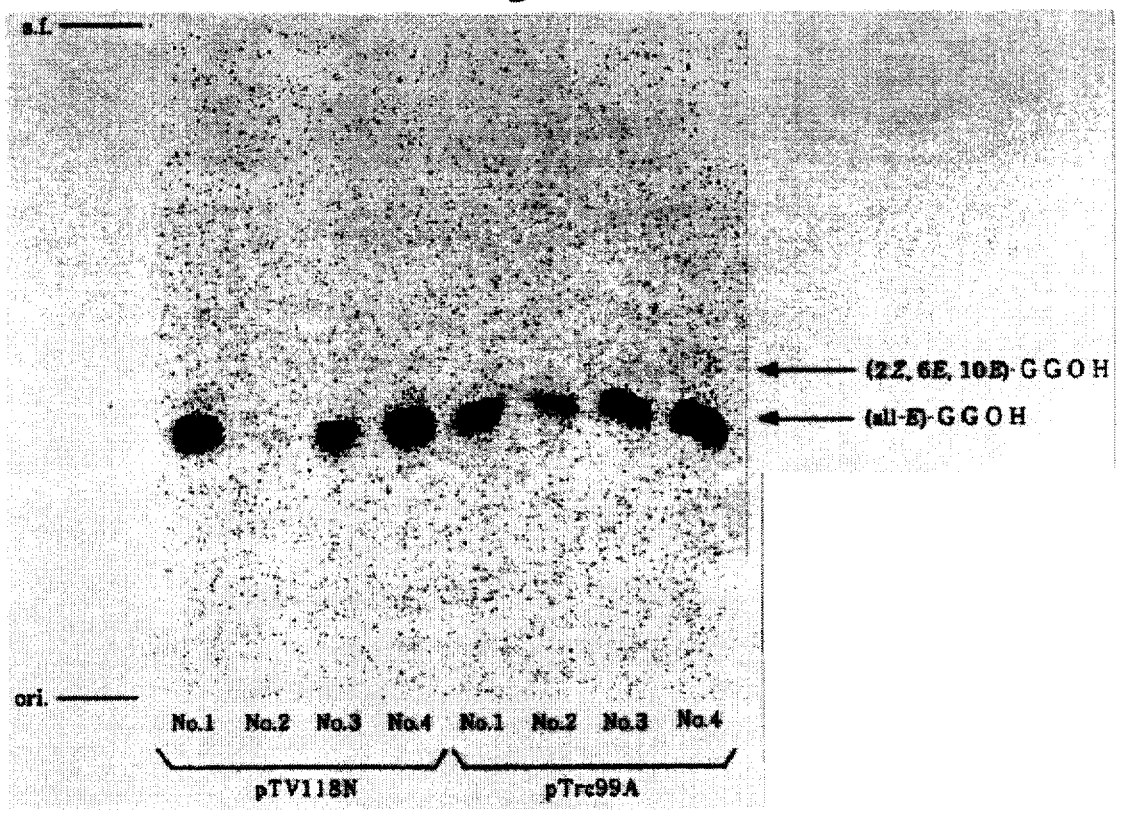
FIG. 9 is a profile of a reversed phase TLC (developer: acetone/water =9/1) showing products formed by acting the present enzyme on a substrate (all-E)-farnesyldiphosphate.

Example 1
Construction of mutated genes (FIG. 5)

The translation start codon in plasmid pFE15 (Japanese Unexamined Patent Publication (Kokai) No. 5-219761) containing a gene coding for farnesyldiphosphate synthase of Bacillus stearothermophilus origin was changed to ATG to obtain plasmid pEX11 (J. Biochem. 113, 355–363 (1993)) for overexpression of farnesyldiphosphate synthase, and the plasmid pEX11 was used in the following Examples. The mutation was carried out according to M. Myers et al. (Science, 229, 242–247 (1985)).

First, a farnesyldiphosphate synthase gene present in NcoI-HindIII fragment in pEX11 was removed, and inserted it into plasmid pTV118N (available from Takara Shuzo, Japan) to construct a plasmid, which was then introduced into E. coli cells. The transformed E. coli cells were cultured. With infection of a helper phage M13K07 (available from Takara Shuzo), pTV118N is converted to a single-stranded DNA and preferentially incorporated in phage particles and liberated out of cells. The culture was centrifuged to obtain a supernatant, from which the single-stranded DNA was recovered.

The single-stranded DNA thus recovered was subjected to mutation with sodium nitrite (concentration 1M or 0.2M) to introduce random mutation into the single-stranded DNA, which was then restored to a double-stranded DNA using AMV reverse-transcriptase XL (E.C.2.7.7.7). This farnesyldiphosphate synthase gene fragment was introduced into pTrc99A (available for Pharmacia) and pTV118N, and resulting recombinant plasmids were used to transform E. coli into which a phytoene synthase gene and phytoene desaturase gene had been previously introduced, and red colonies were selected. The principle of the selection is as follows.

The following screening method follows Ohnuma et al. (J. Biol. Chem., 269, 14792–14797 (1994)). E. coli harboring a plasmid pACYC-IB, into which crtB (phytoene synthase gene) and crtI (phytoene desaturase gene) of a phytopathogen Erwinia uredovora origin had been introduced, was transformed with the mutant plasmid. Note that at present it is believed that E. coli does not have a geranylgeranyl-diphosphate synthase. If the mutant plasmid encodes geranylgeranyldiphosphate synthase activity, lycopene having red color is produced in E. coli cells by pACYC-IB resulting in formation of red-colored colonies. However, if the mutant plasmid does not encode geranylgeranyldiphosphate synthase activity, colonies are color-less. In this way, geranylgeranyldiphosphate synthase activity was easily detected by visual observation.

As a result of transformation of the E. coli cells with the mutant plasmid, red colonies were detected. The ratio of positive clones was $1.32 \times 10^{-3}$ (10 colonies per 7,600 colonies) when the mutation was carried out using 1M $NaNO_2$, while the ratio of positive clones was $5.98 \times 10^{-5}$ (one colony per 16,720 colonies) when the mutation was carried out using 0.2M $NaNO_2$, revealing that the higher the concentration of $NaNO_2$, the higher the positive ratio.

Among the positive colonies, four colonies were selected, and a nucleotide sequence of an enzyme-coding region in the plasmid was determined, and an amino acid sequence encoded by the nucleotide sequence was determined, for each positive clone. The result is shown in SEQ ID NOs: 1 to 4. In addition, these amino acid sequences were compared with the native amino acid sequence, and positions of the mutation are shown in FIG. 4.

Four mutated enzymes encoded by four mutant genes were further characterized.

Example 2

Production of mutated enzymes E. coli transformed with the mutant plasmid was cultured in LB medium at 37° C. overnight. The culture was centrifuged at 3,000×G, at 4° C. for 5 minutes to collect cells, which were then suspended in a buffer for sonication (50 mM Tris-HCl (pH 7.0), 10 mM 2-mercaptoethanol, 1 mM EDTA). The suspension was subjected to ultrasonic waves to disrupt the cells. The sonicate was centrifuged at 5,000×g, at a temperature of 4° C. for 20 minutes, to obtain a supernatant, which was then heated at 55° C. for one hour to inactivate enzymes intrinsic to E. coli to obtain a crude enzyme extract.

To test the enzymatic activity of each mutant enzyme, reactions were carried out in the following reaction mixture.

TABLE 1

| | |
|---|---|
| [1–14C]IPP (1 Ci/mol)) | 25 nmol |
| Allyl substrate (DMAPP, GPP, FPP) | 25 nmol |
| $MgCl_2$ | 5 μmol |
| $NH_4Cl$ | 50 μmol |
| 2-Mercaptoethanol | 50 μmol |
| Tris-HCl buffer (pH 8.5) | 50 μmol |
| Sample to be tested | proper quantity |
| Total | 1 ml |

Note:

DMAPP: Dimethylallyldiphosphate

GPP: Geranyldiphosphate

FPP: Farnesyldiphosphate

The reaction mixture was incubated at 55° C. for 30 minutes, and the product was extracted with water-saturated 1-butanol, and radioactivity of the extract was counted by a liquid scintillation counter. In addition, the extract (butanol layer) was treated with an acid phosphatase and extracted with pentane. The extract was analyzed by TLC. The TLC analysis showed that the use of dimethylallyldiphosphate and geranyldiphosphate as an allyl substrate provides similar TLC patterns. Note that since the amount of each sample was adjusted so that the radioactivity is approximately same between the samples, the density of the band does not indicate specific activity.

The modified enzymes Nos. 1 and 4 produced an amount of geranylgeranyldiphosphate more than that of farnesyldiphosphate, and therefore it is considered that the modified enzymes Nos. 1 and 4 are suitable for the production of geranylgeranyldiphosphate. On the other hand, the modified enzymes No. 2 and No. 3 provided a small amount of geranylgeranyldiphosphate.

Where (all-E)-farnesyldiphosphate was used as a substrate (primer), (all-E)-geranylgeranyldiphosphate was formed. The results are shown in FIGS. 6 to 9.

Specific activity and ratio of product (GGOH/FOH) are shown in Table 2.

TABLE 2

| | Specific activity* (nmol/min/mg protein) | Ratio of product (GGPP/FPP) |
|---|---|---|
| Wild type | 286 | 0 |
| No. 1 pTV118N | 0.293 | 18.4 |
| pTrc99A | 0.253 | 6.28 |
| No. 2 pTV118N | 110 | $2.95 \times 10^{-2}$ |
| pTrc99A | 83 | $2.54 \times 10^{-2}$ |

TABLE 2-continued

|  |  | Specific activity* (nmol/min/mg protein) | Ratio of product (GGPP/FPP) |
|---|---|---|---|
| No. 3 | pTV118N | 143 | $1.65 \times 10^{-1}$ |
|  | pTrc99A | 19.7 | $1.73 \times 10^{-1}$ |
| No. 4 | pTV118N | 0.262 | 15.5 |
|  | pTrc99A | 0.271 | 8.28 |

*DMAPP was used as substrate.

---

We claim:

1. A process for the production of a gene coding for a mutated farnesyldiphosphate synthase capable of synthesizing geranylgeranyl diphosphate comprising the steps of:
   (1) subjecting an unmodified gene coding for a farnesyldiphosphate synthase endogenous to *Bacillus stearothermophilus* to mutagenesis;
   (2) expressing the gene subjected to the mutagenesis in an unicellular host cell; and
   (3) selecting a gene coding for a mutated farnesyldiphosphate synthase capable of synthesizing geranylgeranyl diphosphate wherein at least two amino acids present in the amino acid sequence of the product expressed with the unmodified gene coding for farnesyldiphosphate synthase are substituted with another amino acid at two or more positions selected from the group consisting of 34, 59, 81, 157, 182, 239, 265 and 275.

2. An isolated gene coding for a mutated farnesyldiphosphate synthase capable of synthesizing geranylgeranyldiphosphate, produced by the process of claim 1.

3. A process for production of a mutated farnesyldiphosphate synthase capable of synthesizing a geranylgeranyldiphosphate, comprising the step of expressing the gene of claim 2 in a unicellular host transformed with said gene.

4. A mutated farnesyldiphosphate synthase capable of synthesizing geranylgeranyldiphosphate, produced by the a process of claim 3.

5. A process for production of geranylgeranyldiphosphate or geranylgeranyol, comprising the step of contacting a mutated farnesyldiphosphate synthase capable of synthesizing geranylgeranyldiphosphate with a substrate selected from the group consisting of isopentenyldiphosphate, dimethylallyldiphosphate, geranyldiphosphate and farnesyldiphosphate, wherein an amino acid in the amino acid sequence of the mutated farnesyldiphosphate synthase is substituted with an amino acid other than the corresponding amino acid of unmodified *Bacillus stearothermophilus* farnesyldiphosphate synthase at at least two positions selected from the group consisting of 34, 59, 81, 157, 182, 239, 265 and 275.

6. A modified geranylgeranyldiphosphate synthase having from one to six amino acid positions in an original amino acid sequence of a geranylgeranyldiphosphate synthase modified by a substitution of a different naturally-occurring amino acid wherein, (1) said original amino acid sequence is selected from the group consisting of SEQ ID NO:6, SEQ ID NO:7, SEQ ID NO:8, and SEQ ID NO:9;

(2) said position for an amino acid substitution is located within one or more of the amino acid sequence regions selected from the group consisting of amino acid residues 1 through 38, 53 through 72, 104 through 114, 124 through 158, 165 through 185, 205 through 216, and 251 through 284 of an amino acid sequence of SEQ ID NO:6, SEQ ID NO:7, SEQ ID NO:8, or SEQ ID NO:9;

(3) said amino acid substitution does not result in an amino acid sequence of any of SEQ ID NO:6, SEQ ID NO:7, SEQ ID NO:8, or SEQ ID NO:9; and (4) said modified geranylgeranyldiphosphate synthase retains the activity of a geranylgeranyldiphosphate synthase.

7. A mutated geranylgeranyldiphosphate synthase having a mutation at at least two of the amino acid positions selected from the group consisting of position 34, 59, 81, 157, 182, 239, 265 and 275 of *Bacillus stearothermophilus* farnesyldiphosphate synthase.

8. A modified geranylgeranyldiphosphate synthase having an amino acid sequence shown in SEQ ID NO:6.

9. A modified geranylgeranyldiphosphate synthase having an amino acid sequence shown in SEQ ID NO:7.

10. A modified geranylgeranyldiphosphate synthase having an amino acid sequence shown in SEQ ID NO:8.

11. A modified geranylgeranyldiphosphate synthase having an amino acid sequence shown in SEQ ID NO:9.

12. An isolated gene coding for a geranylgeranyldiphosphate synthase according to claim 6.

13. An isolated gene coding for a geranylgeranyldiphosphate synthase according to claim 7.

14. An isolated gene coding for a geranylgeranyldiphosphate synthase according to claim 8.

15. An isolated gene coding for a geranylgeranyldiphosphate synthase according to claim 9.

16. An isolated gene coding for a geranylgeranyldiphosphate synthase according to claim 10.

17. An isolated gene coding for a geranylgeranyldiphosphate synthase according to claim 11.

18. An expression vector comprising a gene according to claim 12.

19. An expression vector comprising a gene according to claim 13.

20. An expression vector comprising a gene according to claim 14.

21. An expression vector comprising a gene according to claim 15.

22. An expression vector comprising a gene according to claim 16.

23. An expression vector comprising a gene according to claim 17.

24. A unicellular recombinant host transformed with an expression vector according to claim 18.

25. A unicellular recombinant host transformed with an expression vector according to claim 19.

26. A unicellular recombinant host transformed with an expression vector according to claim 20.

27. A unicellular recombinant host transformed with an expression vector according to claim 21.

28. A unicellular recombinant host transformed with an expression vector according to claim 22.

29. A unicellular recombinant host transformed with an expression vector according to claim 23.

* * * * *